(12) United States Patent
Fukuhara et al.

(10) Patent No.: US 12,319,633 B2
(45) Date of Patent: Jun. 3, 2025

(54) METHANE PRODUCING METHOD AND PRODUCTION SYSTEM

(71) Applicants: NATIONAL UNIVERSITY CORPORATION SHIZUOKA UNIVERSITY, Shizuoka (JP); Amano Institute of Technology, Hamamatsu (JP)

(72) Inventors: Choji Fukuhara, Hamamatsu (JP); Masao Sudoh, Hamamatsu (JP); Hiroshi Akama, Hamamatsu (JP)

(73) Assignees: NATIONAL UNIVERSITY CORPORATION SHIZUOKA UNIVERSITY (JP); AMANO INSTITUTE OF TECHNOLOGY (JP)

( * ) Notice: Subject to any disclaimer, the term of this patent is extended or adjusted under 35 U.S.C. 154(b) by 598 days.

(21) Appl. No.: 17/639,353

(22) PCT Filed: Sep. 2, 2020

(86) PCT No.: PCT/JP2020/033257
§ 371 (c)(1),
(2) Date: Mar. 1, 2022

(87) PCT Pub. No.: WO2021/045101
PCT Pub. Date: Mar. 11, 2021

(65) Prior Publication Data
US 2022/0298086 A1    Sep. 22, 2022

(30) Foreign Application Priority Data
Sep. 3, 2019    (JP) .................................. 2019-160190

(51) Int. Cl.
*C07C 1/12*    (2006.01)
*B01J 8/02*    (2006.01)
*B01J 8/04*    (2006.01)

(52) U.S. Cl.
CPC ............... *C07C 1/12* (2013.01); *B01J 8/0285* (2013.01); *B01J 8/0438* (2013.01); *B01J 8/0496* (2013.01); *B01J 2208/00309* (2013.01)

(58) Field of Classification Search
CPC ..... C07C 1/12; C07C 9/04; C10G 2/32; B01J 23/755; B01J 23/83
See application file for complete search history.

(56) References Cited

U.S. PATENT DOCUMENTS 3,852,180 A * 12/1974 Gregory .................... C25B 1/00
518/728
2013/0041051 A1    2/2013 Zuberbuhler et al. ........ 518/712
(Continued)

FOREIGN PATENT DOCUMENTS

CN    1789111 A    6/2006
GB    1042366 A    9/1966
(Continued)

OTHER PUBLICATIONS

International Search Report mailed Nov. 2, 2020 in corresponding PCT International Application No. PCT/JP2020/033257.
(Continued)

*Primary Examiner* — Jafar F Parsa
(74) *Attorney, Agent, or Firm* — OSTROLENK FABER LLP (57) ABSTRACT

A method for producing methane that includes supplying a raw material gas containing hydrogen gas, oxygen gas, and carbon dioxide gas to a reactor provided with a catalyst, thereby starting a methanation reaction using heat including reaction heat due to catalyst combustion of the hydrogen gas; and continuing the methanation reaction.

8 Claims, 4 Drawing Sheets

(56) References Cited

U.S. PATENT DOCUMENTS

| | | | | |
|---|---|---|---|---|
| 2014/0200279 | A1* | 7/2014 | Wang | B01J 37/04 518/715 |
| 2017/0022121 | A1* | 1/2017 | Abbott | C07C 1/12 |

FOREIGN PATENT DOCUMENTS

| | | | |
|---|---|---|---|
| JP | H10-185170 | A | 7/1998 |
| JP | 2013-515684 | A | 5/2013 |
| JP | 2015-007039 | A | 1/2015 |
| JP | 2018-168205 | A | 11/2018 |
| JP | 2019-142808 | A | 8/2019 |
| JP | 2019-155227 | A | 9/2019 |
| JP | 2020-033280 | A | 3/2020 |
| JP | 2020-037535 | A | 3/2020 |
| WO | WO 2011/076315 | A2 | 6/2011 |
| WO | WO 2015/159044 | A1 | 10/2015 |

OTHER PUBLICATIONS

English translation of the International Preliminary Report on Patentability (IPRP) (Chapter 1) mailed Mar. 17, 2022 with a Notification from the International Bureau (Form PCT/IB/338) in corresponding PCT International Application No. PCT/JP2020/033257.

Fukuhara, Choji et al., "Auto-methanation of Carbon Dioxide: A Novel Route for Transforming CO2 over Ni-based Catalyst", *Chemistry Letters*, 2019, 48 (3), pp. 196-199.

Fukuhara, Choji et al., "Auto-methanation Performance of Structured Ni-type Catalyst for CO2 Transformation", *Chemistry Letters*, 2019, 48 (5), pp. 441-444.

Fukuhara, Choji et al., "Auto-methanation for transition-metal catalysts loaded on various oxide supports: A novel route for CO2 transformation at room-temperature and atmospheric pressure"; *Chemical Engineering Science*, 2020, vol. 219, 115589, pp. 1-14.

Fukuhara, Choji et al., "Auto-methanation of CO2 on supported Ni-series metal catalyst under a room temperature atmosphere", *Proceedings of the forum A of Catalysis Society of Japan Meeting*, Sep. 11, 2019, vol. $124^{th}$, and partial translation.

Hirata, Nozomu et al., "Auto-methanation of CO2 catalyzed by Ru/CeO2", *Lecture preprints of the forum of Catalysis Society of Japan Meeting*, Mar. 10, 2020, vol. $125^{th}$, and partial translation.

Akama, Hiroshi et al., "Effect of produced water and oxygen concentration on auto-methanation of carbon dioxide", *Proceedings of the forum A of Catalysis Society of Japan Meeting*, Sep. 11, 2019, vol. $124^{th}$, and partial translation.

Lu, Chaohao et al.: "Effect of Hydrogen on Catalytic Combustion of Methane with Ultra-low Concentrations", Journal of Chinese Society of Power Engineering, vol. 36, No. 4, Apr. 2016, p. 271-p. 276. English translation of the Abstract.

* cited by examiner

METHANE PRODUCING METHOD AND PRODUCTION SYSTEM

CROSS-REFERENCE TO RELATED APPLICATIONS

The present application is a 35 U.S.C. §§ 371 national phase conversion of International Application No. PCT/JP2020/033257, filed Sep. 2, 2020, which claims priority to Japanese Patent Application No. 2019-160190, filed Sep. 3, 2019, the contents of both of which are incorporated herein by reference. The PCT International Application was published in the Japanese language.

TECHNICAL FIELD

The present invention relates to a method for producing methane and a production system for producing methane.

BACKGROUND ART

In the related art, it has been examined that emission of carbon dioxide is suppressed by converting carbon dioxide, which is abundantly contained in industrial exhaust gas of thermal power plants, steelworks, and the like, into methane. Therefore, a reaction called a methanation reaction for producing methane and water from carbon dioxide and hydrogen as in the following reaction formula is used (for example, Patent Literature 1).

$$CO_2 + 4H_2 \rightarrow CH_4 + 2H_2O$$

CITATION LIST

Patent Literature

[Patent Literature 1] Japanese Unexamined Patent Publication No. 2018-168205

SUMMARY OF INVENTION

Technical Problem

An exhaust gas containing carbon dioxide may also contain oxygen. For example, in many cases, exhaust gases discharged from thermal power plants generally contain about 4 to 15 volume % oxygen gas. When oxygen is present in an exhaust gas, a catalyst metal binds to the oxygen to produce a metal oxide, and thus the catalyst is easily deactivated. For this reason, in the case of a methanation reaction in which an exhaust gas containing oxygen is used as a raw material gas, it is necessary to remove the oxygen from the exhaust gas in advance. However, from the viewpoint of simplification of manufacturing facilities, it is desirable to enable the step of removing oxygen to be omitted. In addition, it is also desirable to enable saving on energy costs of heating required to start a reaction.

Therefore, an object of one aspect of the present invention is to efficiently produce methane without requiring removal of oxygen in advance from a raw material gas containing carbon dioxide and oxygen and to reduce energy costs required for heating for the production.

Solution to Problem

According to one aspect of the present invention, there is provided a method for producing methane, including: supplying a raw material gas containing hydrogen gas, oxygen gas, and carbon dioxide gas to a reactor provided with a catalyst, thereby starting a methanation reaction using heat including reaction heat due to catalyst combustion of the hydrogen gas; and continuing the methanation reaction.

According to another aspect of the present invention, there is provided a production system for producing methane from a raw material gas containing carbon dioxide, hydrogen, and oxygen through a methanation reaction, the system including: a reactor; a catalyst provided in the reactor; a hydrogen supply line that supplies hydrogen gas to the reactor; an air supply line that supplies air containing oxygen gas to the reactor; and an exhaust gas supply line that supplies an exhaust gas containing carbon dioxide gas to the reactor, wherein the catalyst includes a catalyst functioning as a catalyst for both a methanation reaction and combustion of the hydrogen gas, or a first catalyst for hydrogen gas combustion and a second catalyst for a methanation reaction.

Advantageous Effects of Invention

According to one aspect of the present invention, it is possible to efficiently produce methane without requiring removal of oxygen in advance from a raw material gas containing carbon dioxide and oxygen and to reduce energy costs required for heating for the production.

DESCRIPTION OF EMBODIMENTS

Hereinafter, some embodiments of the present invention will be described in detail. However, the present invention is not limited to the following embodiments.

One embodiment of a method for producing methane includes: supplying a raw material gas containing hydrogen gas, oxygen gas, and carbon dioxide gas to a reactor provided with a catalyst, thereby starting a methanation reaction using heat including reaction heat due to catalyst combustion of the hydrogen gas; and continuing the methanation reaction.

Figure 1:
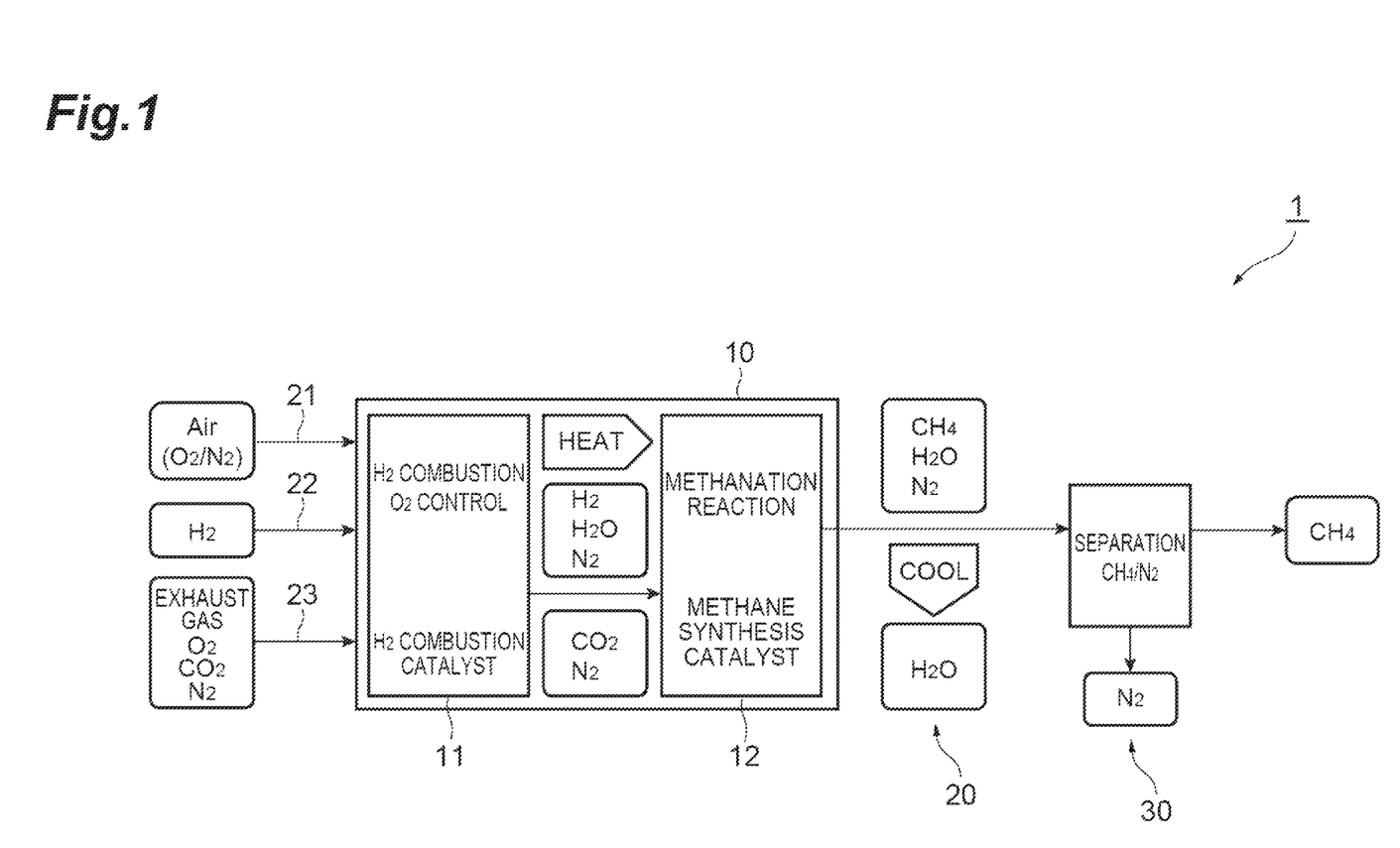
FIG. 1 is a configuration diagram illustrating an example of a production system for producing methane.

FIG. 1 is a configuration diagram illustrating an example of a production system for producing methane through the above-described method. A production system 1 shown in FIG. 1 includes: a reactor 10 provided with a catalyst; an air supply line 21 for supplying air containing oxygen gas and nitrogen gas; a hydrogen supply line 22 for supplying a gas containing hydrogen gas; and an exhaust gas supply line 23 for supplying an exhaust gas containing carbon dioxide gas and oxygen gas. The air may be an air incorporated from atmospheric air. That is, some or all of the oxygen gas in the raw material gas may be gas supplied by introducing air. The exhaust gas may further contain nitrogen gas.

As catalysts, a first catalyst ($H_2$ combustion catalyst) for hydrogen gas combustion and a second catalyst (methane synthesis catalyst) for a methanation reaction are provided in a reactor 10. The reactor 10 includes a first reaction chamber 11 and a second reaction chamber 12 that are capable of exchanging heat with each other, the first catalyst is provided in the first reaction chamber 11, and the second catalyst is provided in the second reaction chamber 12.

The reactor 10 forms a gas flow path in which a gas introduced into the first reaction chamber 11 passes through the second reaction chamber 12 and is then discharged outside the reactor 10. The air supply line 21, the hydrogen supply line 22, and the exhaust gas supply line 23 are connected to this gas flow path. The raw material gas containing carbon dioxide gas, hydrogen gas, and oxygen gas is introduced into the gas flow path of the reactor 10 due to the gas supplied from the air supply line 21, the hydrogen supply line 22, and the exhaust gas supply line 23.

The raw material gas may not always contain all of carbon dioxide gas, hydrogen gas, and oxygen gas during production of methane. For example, in the method for producing methane using the production system 1, a raw material gas containing oxygen gas and nitrogen gas supplied from the air supply line 21 and hydrogen gas supplied from the hydrogen supply line 22 may be supplied to the reactor 10, and then carbon dioxide gas may be introduced from the exhaust gas supply line 23 into the reactor 10 after the catalyst combustion of the hydrogen gas is started in the first reaction chamber 11, thereby supplying the raw material gas containing hydrogen gas, oxygen gas, and carbon dioxide gas to the reactor 10. The supply of hydrogen gas from the hydrogen supply line 22 and oxygen gas from the air supply line 21 to the reactor 10 may be started in that order.

When the catalyst combustion of hydrogen gas is started in the first reaction chamber 11, nitrogen gas is sent as a carrier gas to the second reaction chamber 12 with heat together with the remaining hydrogen gas and produced water. As a result, the temperature of the second catalyst (methane synthesis catalyst) in the second reaction chamber 12 increases. When the temperature of the second catalyst exceeds a predetermined temperature, for example, 100° C. (or 220° C.), it is determined that a methanation reaction of carbon dioxide can be started. At start-up when catalyst combustion of hydrogen gas is started, the raw material gas is usually formed by a gas supplied from the air supply line 21 and the hydrogen supply line 22. The temperature of a gas in the vicinity of a catalyst may be regarded as the temperature of the catalyst.

After confirming that a methanation reaction of carbon dioxide can be started, carbon dioxide gas is supplied to the reactor 10 from the exhaust gas supply line 23 and is introduced into the second reaction chamber. The exhaust gas from the exhaust gas supply line 23 may be directly introduced into the second reaction chamber 12 without passing through the first reaction chamber 11. In the second reaction chamber 12, a methanation reaction of carbon dioxide is started due to reaction heat including heat due to the catalyst combustion of hydrogen gas and continues thereafter. A product gas containing methane produced by the methanation reaction is discharged outside the reactor 10.

The production system 1 may include a cooling device 20 provided downstream of the reactor 10. Water produced together with methane by a methanation reaction is removed by the cooling device 20. The production system 1 may further include a separator 30 which is provided downstream of the reactor 10 and separates methane and nitrogen. With these devices, it is possible to increase the concentration of methane in the product gas. The collected methane can be used as, for example, a fuel such as city gas.

Figure 2:
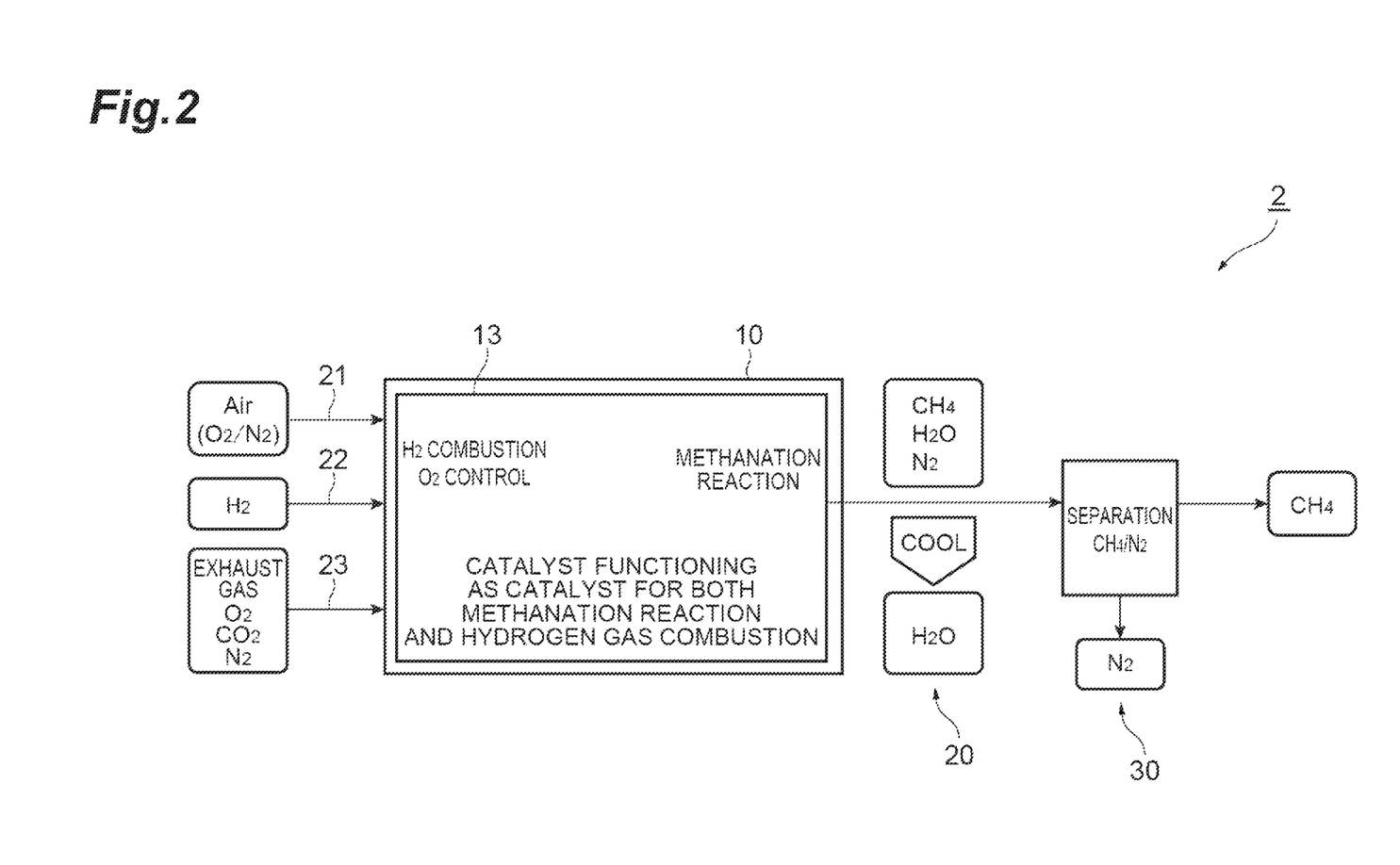
FIG. 2 is a configuration diagram illustrating another example of a production system for producing methane.

Another embodiment of the method for producing methane is carried out using a production system 2 shown in FIG. 2. The production system 2 includes a single reaction chamber 13 instead of the first reaction chamber 11 and the second reaction chamber 12 as in the production system 1 shown in FIG. 1, and a catalyst (third catalyst) functioning as a catalyst for both a methanation reaction and hydrogen gas combustion is provided in the reaction chamber 13.

The raw material gas may not always contain all of carbon dioxide gas, hydrogen gas, and oxygen gas during production of methane. For example, in the method for producing methane using the production system 2, a raw material gas containing oxygen gas and nitrogen gas supplied from the air supply line 21 and hydrogen gas supplied from the hydrogen supply line 22 may be supplied to the reactor 10, and then carbon dioxide gas may be introduced from the exhaust gas supply line 23 into the reactor 10 after the catalyst combustion of hydrogen gas is started in the reaction chamber 13, thereby supplying the raw material gas containing hydrogen gas, oxygen gas, and carbon dioxide gas to the reactor 10. The supply of hydrogen gas from the hydrogen supply line 22 and oxygen gas from the air supply line 21 to the reactor 10 may be started in that order.

When the catalyst combustion of hydrogen gas is started in the reaction chamber 13, heat is generated, and the temperatures of the reaction chamber 13 and the third catalyst increase. When the temperature of the third catalyst exceeds a predetermined temperature, for example, 100° C. (or 220° C.), it is determined that a methanation reaction of carbon dioxide can be started. At start-up when catalyst combustion of hydrogen gas is started, the raw material gas is usually formed by a gas supplied from the air supply line 21 and the hydrogen supply line 22. The temperature of a gas in the vicinity of a catalyst may be regarded as the temperature of the catalyst.

After confirming that a methanation reaction of carbon dioxide can be started, carbon dioxide gas is supplied to the reactor 10 from the exhaust gas supply line 23. In the reaction chamber 13, a methanation reaction of carbon dioxide is started due to reaction heat including heat due to the catalyst combustion of hydrogen gas and continues thereafter. A product gas containing methane produced by the methanation reaction is discharged outside the reactor 10.

In the related art, in order to obtain high-purity methane, a method has been used in which carbon dioxide gas in an exhaust gas is once separated and collected to form high-purity carbon dioxide and is made to react with hydrogen gas. Devices for separating and collecting carbon dioxide are relatively large, and in the case of a methanation reaction of high-purity carbon dioxide, reaction heat is likely to be localized in a catalyst, which may cause thermal runaway. The method according to the present embodiment is advantageous from the viewpoint that these problems can be avoided.

Figure 3:
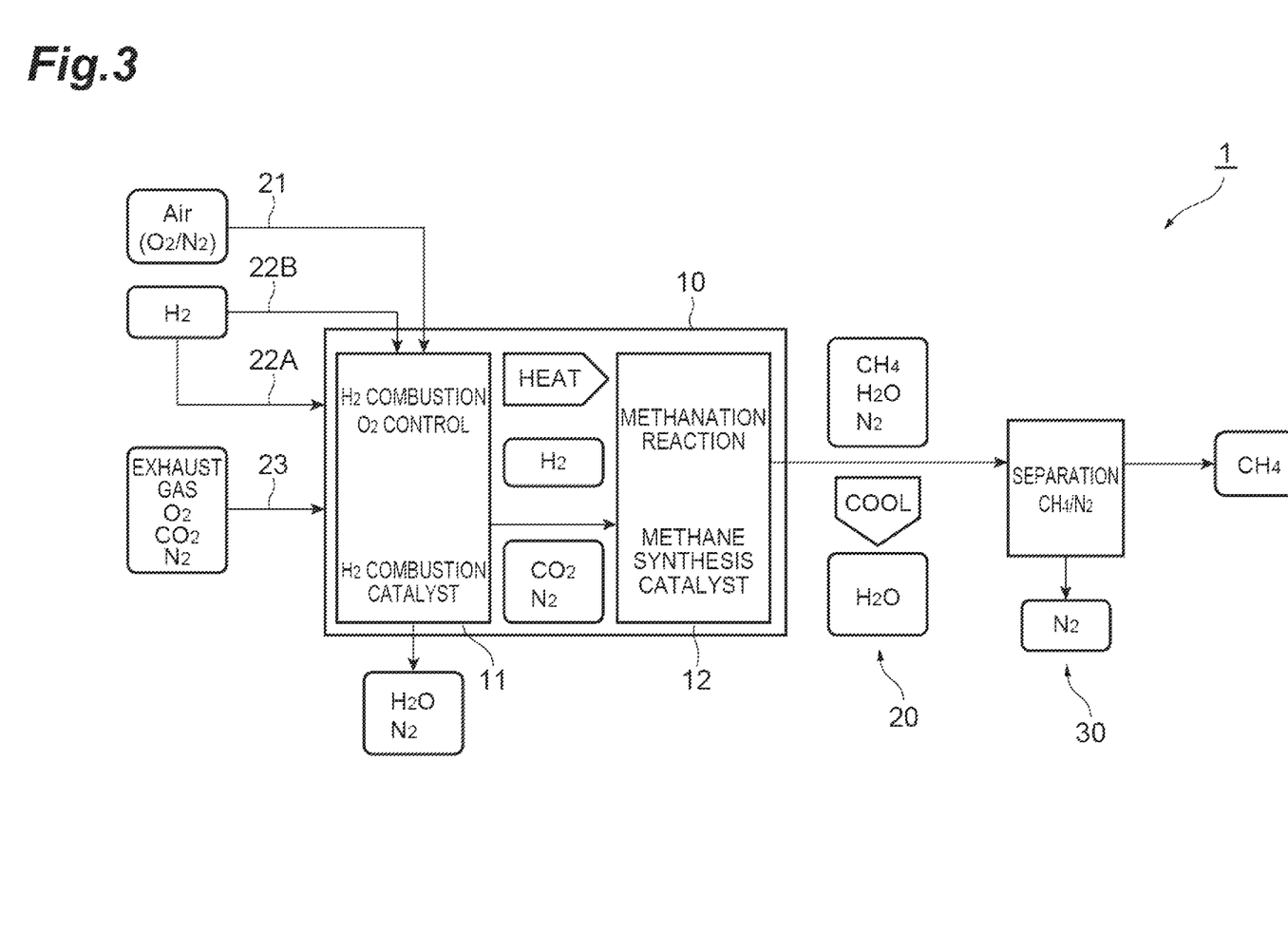
FIG. 3 is a configuration diagram illustrating still another example of a production system for producing methane.

FIG. 3 is a configuration diagram illustrating still another example of a production system for producing methane. Also in a production system 1 shown in FIG. 3, similarly to the production system of FIG. 1, a first reaction chamber 11 and a second reaction chamber 12 that are capable of exchanging heat with each other are provided in a reactor 10. However, the production system 1 shown in FIG. 3 has a configuration different from the production system of FIG. 1 in that the reactor 10 forms a first gas flow path in which a gas introduced into the first reaction chamber 11 passes through the second reaction chamber 12 and is then discharged outside the reactor and a second gas flow path in which a gas introduced into the first reaction chamber 11 is discharged outside the reactor 10 without passing through the second reaction chamber 12. A hydrogen supply line is divided into two parts, a hydrogen supply line 22A and an exhaust gas supply line 23 are connected to the first flow path, and a hydrogen supply line 22B and an air supply line 21 are connected to the second flow path.

In the production system 1 of FIG. 3, a gas flow path separated into the first gas flow path and the second gas flow path is formed in the reactor 10. At start-up until when catalyst combustion of hydrogen gas is started, a raw material gas is supplied to the second flow path. At start-up, it is necessary to supply oxygen gas at a relatively high concentration, and as a result, a large amount of water is produced. By allowing the produced water to flow through the second gas flow path and discharging it outside the reactor 10, the amount of water flowing into the second reaction chamber 12 can be suppressed. The small amount of water flowing from the first reaction chamber 11 into the second reaction chamber 12 is advantageous for an efficient methanation reaction. In addition, high-purity carbon dioxide gas may be used instead of an exhaust gas containing carbon dioxide. In this case, the high-purity carbon dioxide gas can be prevented from being diluted by air supplied from the air supply line 21.

In a case where methane is produced using the production systems exemplified in FIGS. 1 to 3 or other production systems, the concentrations of hydrogen gas and oxygen gas in a raw material gas can be controlled such that a methanation reaction is started and then continues autonomously. For example, the concentrations of hydrogen gas and oxygen gas in a raw material gas may be controlled based on the temperature of the second catalyst (methane synthesis catalyst) or the third catalyst. If the temperature of a methane synthesis catalyst is increased by heat including reaction heat of catalyst combustion of hydrogen gas, the concentration of oxygen gas required for starting and continuing a methanation reaction can be lowered. The concentrations of hydrogen gas and oxygen gas can be appropriately controlled based on such a relationship between the temperature of a catalyst and the concentration of each gas.

When a methanation reaction starts, reaction heat of the methanation reaction and reaction heat of catalyst combustion of hydrogen gas are combined to cause the temperatures of a catalyst and a gas in a reactor to rise excessively, sometimes resulting in a decrease in the yield of methane. For this reason, the concentration of oxygen gas in a raw material gas may be lowered until the temperature of the second catalyst (methane synthesis catalyst) or the third catalyst reaches a predetermined temperature after a methanation reaction is started, and then may be controlled such that the temperature of the second catalyst (methane synthesis catalyst) or the third catalyst is maintained at a predetermined temperature or higher. The predetermined temperature here also depends on catalysts, and may be, for example, 100° C. to 250° C. or 220° C. to 250° C. By lowering the concentration of oxygen gas, the temperature of the second catalyst or the third catalyst can be lowered. For example, after a methanation reaction has started, air supply from an air supply line may be blocked. In this case, the amount of hydrogen gas supplied may be adjusted to compensate for consumption of hydrogen gas due to catalyst combustion of hydrogen gas produced by oxygen gas in an exhaust gas.

Until a methanation reaction starts, the concentration of hydrogen gas in a raw material gas introduced into a reactor is controlled, for example, within a range of 6 to 40 volume %, and the concentration of oxygen gas therein is controlled, for example, within a range of 0.1 to 30 volume %, 3 to 30 volume %, 0.1 to 20 volume %, 3 to 20 volume %, 0.1 to 10 volume %, or 3 to 10 volume %. During steady operation in which a methanation reaction starts and then continues, the concentration of hydrogen gas in a raw material gas introduced into a reactor is controlled, for example, within a range of 30 to 60 volume %, and the concentration of oxygen gas therein is controlled, for example, within a range of 0.1 to 20 volume %, or 0.1 to 6 volume %. These concentrations are values based on the total volume of raw material gas supplied to a reactor. A raw material gas usually contains an inert gas such as nitrogen gas as a carrier gas. A raw material gas may further contain a small amount of other gases derived from air or the like.

A methanation reaction may be started and continued by heat including heat supplied from an external heat source in addition to reaction heat due to catalyst combustion of hydrogen gas. In this case, the amount of heat supplied from the external heat source is controlled such that a methanation reaction starts and continues. As exemplified in examples to be described below, when the concentration of oxygen gas in a raw material gas is low, there is a tendency that the appropriate amount of heat supplied from the external heat source increases in order to start and continue a methanation reaction. The amount of heat supplied from an external heat source can be suitably controlled based on such a relationship between the concentration of oxygen gas and the amount of heat supplied from the external heat source.

The amount of heat supplied from an external heat source is adjusted, for example, by the set temperature of the heat source. The heat source is not particularly limited, and may be an electric heater generating heat through resistance heating or the like or may be a heat medium heated to a predetermined temperature, for example.

The catalyst provided in a reactor may include a catalyst (third catalyst) functioning as a catalyst for both a methanation reaction and hydrogen gas combustion, or may include a first catalyst for the hydrogen gas combustion and a second catalyst for a methanation reaction. The first catalyst and the second catalyst may be the same as or different from each other.

The catalyst for hydrogen gas combustion may be a catalyst containing a catalytic support or a catalyst metal carried on a catalytic support. Examples of catalytic supports include metal oxides such as alumina ($Al_2O_3$), ceria ($CeO_2$), zirconia ($ZrO_2$), yttrium ($Y_2O_3$), magnesia ($MgO$)), and titania ($TiO_2$) and composite metal oxides thereof, and composite metal oxides such as silica-alumina ($SiO_2$—$Al_2O_3$), various perovskites, and zeolites. Examples of catalyst metals include noble metals such as Rh, Pd, Pt, and Ru, and base metals such as Ni, Co, Cu, Mn, and Fe. A catalyst metal may contain two or more kinds of metals.

The catalyst (catalyst for methane synthesis) for a methanation reaction may be a catalyst containing a catalytic support or a catalyst metal carried on a catalytic support. Examples of catalytic supports include metal oxides such as alumina ($Al_2O_3$), ceria ($CeO_2$), zirconia ($ZrO_2$), yttrium ($Y_2O_3$), magnesia ($MgO$)), and titania ($TiO_2$) and composite metal oxides thereof, and composite metal oxides such as silica-alumina ($SiO_2$—$Al_2O_3$), various perovskites, and zeolites. Examples of catalyst metals include base metals such as Ni, Co, Cu, Mn, and Fe, and noble metals such as Pd, Rh, and Ru. A catalyst metal may contain two or more kinds of metals.

A granular catalyst may be accommodated in a reactor. Alternatively, a catalyst structure including a metal molded body and a catalyst layer that is formed on the metal molded body and contains the catalyst, a so-called monolithic catalyst, may be accommodated in a reactor. The method according to the present embodiment is sometimes accompanied by a significant temperature rise of a catalyst, and a methanation reaction is an exothermic reaction. However, accumulation of an excessive amount of heat is likely to be avoided by providing a catalyst layer on a metal molded body having a high dissipation effect compared to, for example, a catalyst having a ceramic catalytic support. The metal molded body may be a plate-like body or a plate-like body processed into a twist shape. The plate-like body processed into a twist shape is a plate-like molded body extending along a constant axis while twisting in a direction of rotation around the axis. Since the monolithic catalyst having a twisted plate-like body has excellent characteristics in terms of heat dissipation and contact with a gas, if this is used, excellent yield of methane is likely to be realized even with a relatively small amount of catalyst. The metal molded body may be, for example, an aluminum molded body.

Examples

Hereinafter, the present invention will be described more specifically with reference to the examples. However, the present invention is not limited to these examples.

1. Production of Catalyst

Cerium oxide powder was added to an aqueous solution of nickel nitrate hexahydrate and stirred, and then water was evaporated from the dispersion liquid while heating. The remaining powder was held overnight in a dryer at 150° C., and then fired in atmospheric air at 500° C. for 2 hours using an electric furnace to obtain powders of cerium oxide and catalyst particles ($Ni/CeO_2$) containing nickel carried on the cerium oxide. The content of nickel in these catalyst particles is 10 mass % based on the mass of cerium oxide. The powder of catalyst particles was compression-molded, and the obtained molded body was pulverized. A granular catalyst having a particle size of 30 to 60 meshes was obtained from the pulverized product using a sieve.

2. Methanation Reaction

Test 1

A glass reaction tube (with an inner diameter of 8.0 mm and an outer diameter of 10.0 mm) of a normal-pressure fixed-bed flow type microreactor was filled with 0.3 g of the obtained catalyst to form a catalyst layer. The reaction tube was provided in an electric furnace. Each supply line for carbon dioxide, hydrogen, oxygen, or nitrogen gas was connected to the reaction tube. Each supply line was equipped with a mass flow controller for controlling the flow rate and a flowmeter.

The temperature of the electric furnace in which the reaction tube was provided was held at 25° C., and nitrogen ($N_2$) gas was passed through the catalyst layer at a flow rate of 180 mL/min. In this state, when hydrogen ($H_2$) gas and oxygen ($O_2$) gas were further passed in this order at respective flow rates of 200 mL/min and 20 mL/min, the temperature of the catalyst layer rose sharply due to reaction heat of catalyst combustion of hydrogen. Subsequently, when carbon dioxide ($CO_2$) gas was further supplied at a flow rate of 40 mL/min while maintaining the flow rates of nitrogen gas, hydrogen gas, and oxygen gas, a methanation reaction started, the temperature of the catalyst layer rose to 500° C., and the methanation reaction continued. The concentration of $CO_2$ of a product gas flowing out of the reaction tube during the methanation reaction was quantitatively determined, and a conversion ($CO_2$ conversion) rate from $CO_2$ to methane was obtained from the measurement result.

Tests 2 to 6

Methanation reaction tests were performed in the same manner as in Test 1 except that the flow rate of oxygen gas was changed to 0 mL/min, 2 mL/min, 4 mL/min, 8 mL/min, or 12 mL/min. However, since no start of a methanation reaction was confirmed at a set temperature of 25° C. of the electric furnace provided with a reaction tube, the set temperature of the electric furnace was adjusted such that a methanation reaction starts and continues. Set temperatures of electric furnaces at which the start and continuation of a methanation reaction are confirmed are shown in Table 1. The concentration of $CO_2$ of a product gas flowing out of the reaction tube during the methanation reaction was quantitatively determined, and a conversion rate (conversion rate of $CO_2$) from $CO_2$ to methane was obtained from the measurement result.

TABLE 1

| | | Test 1 | Test 2 | Test 3 | Test 4 | Test 5 | Test 6 |
|---|---|---|---|---|---|---|---|
| Catalyst | | | | $Ni/CeO_2$ | | | |
| Flow rate [mL/min] | $N_2$ | 180 | 188 | 192 | 196 | 198 | 200 |
| | $H_2$ | 200 | 200 | 200 | 200 | 200 | 200 |
| | $O_2$ | 20 | 12 | 8 | 4 | 2 | 0 |
| | $CO_2$ | 40 | 40 | 40 | 40 | 40 | 40 |
| $O_2$ Concentration [volume %] | | 5 | 3 | 2 | 1 | 0.5 | 0 |
| Electric furnace set temperature [° C.] | | 25 | 56 | 70 | 120 | 135 | 220 |

Figure 4:
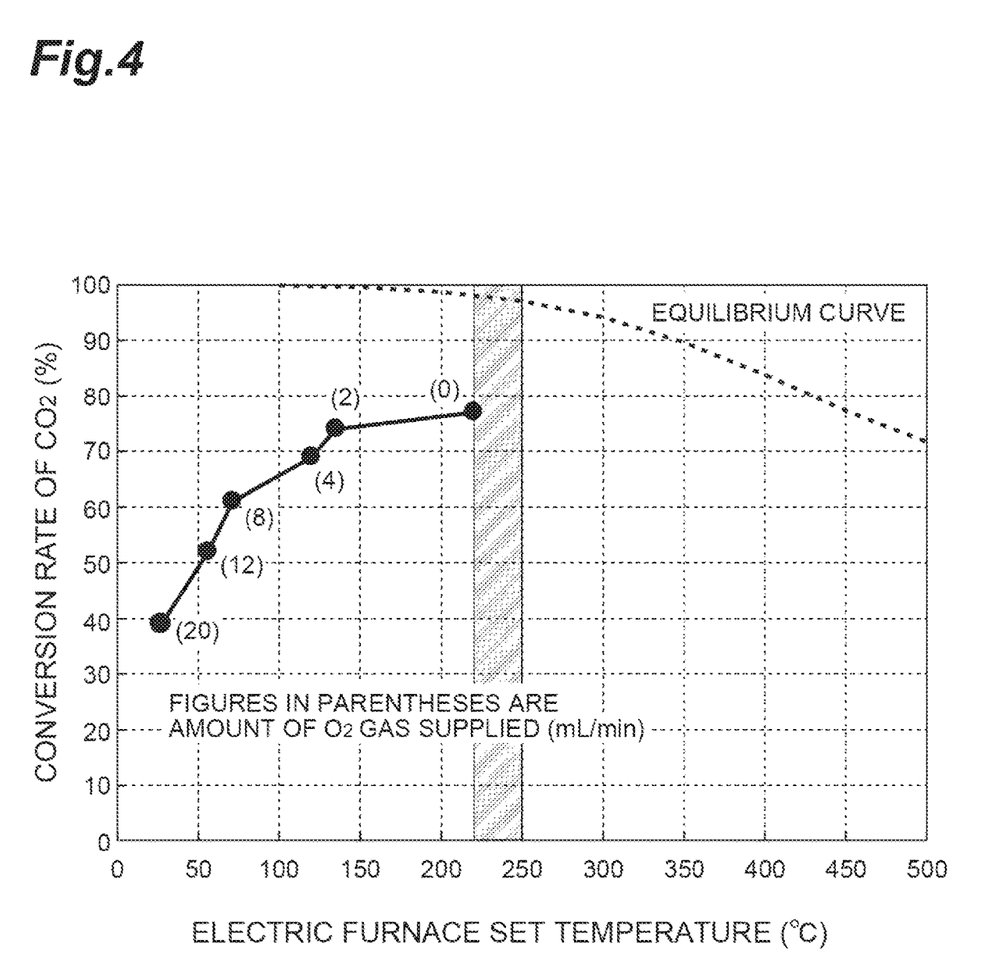
FIG. 4 is a graph illustrating a relationship between an electric furnace set temperature and a conversion rate of carbon dioxide due to a methanation reaction.

FIG. 4 is a graph illustrating a relationship between a conversion rate of $CO_2$ and an electric furnace set temperature at which a methanation reaction starts and continues. By appropriately controlling the concentration of each component of a raw material gas and as necessary the heating conditions using an external heat source with reference to the relationship shown in FIG. 4 and the like, a methanation reaction can be efficiently performed using a raw material gas containing $O_2$. The conversion rate of $CO_2$ in Test 5 in which a raw material gas contains 2 volume % of $O_2$ is slightly lower than that of $CO_2$ in Test 6 in which a raw material gas contains no $O_2$. However, since the yield of $CH_4$ with respect to $CO_2$ is 73% in Test 5 and 75% in Test 6, it can be said that both Tests 5 and 6 are at the same level.

REFERENCE SIGNS LIST 1, 2: Production system, 10: Reactor, 11: First reaction chamber, 12: Second reaction chamber, 13: Reaction chamber

The invention claimed is:
1. A method for producing methane, comprising:
supplying a raw material gas containing hydrogen gas, oxygen gas, and carbon dioxide gas to a reactor provided with a catalyst, thereby starting a methanation reaction using heat including reaction heat due to catalyst combustion of the hydrogen gas; and
continuing the methanation reaction.

2. The method according to claim 1,
wherein a raw material gas containing the hydrogen gas and the oxygen gas is supplied to the reactor, and then a raw material gas further containing the carbon dioxide gas is supplied to the reactor after the catalyst combustion of the hydrogen gas is started.

3. The method according to claim 1,
wherein concentrations of the hydrogen gas and the oxygen gas in the raw material gas is controlled such that the methanation reaction is started and continued.

4. The method according to claim 3,
wherein the concentrations of the hydrogen gas and the oxygen gas in the raw material gas is controlled based on a temperature of the catalyst.

5. The method according to claim 4,
wherein the concentration of the oxygen gas in the raw material gas is lowered until the temperature of the catalyst reaches a predetermined temperature after the methanation reaction is started, and then the temperature of the catalyst is controlled such that the temperature is maintained at the predetermined temperature or higher.

6. The method according to claim 1,
wherein some or all of the carbon dioxide gas is a gas derived from an exhaust gas.

7. The method according to claim 1,
wherein some or all of the oxygen gas is a gas supplied by introducing air containing oxygen gas.

8. The method according to claim 1,
wherein a catalyst structure comprising a metal molded body and a catalyst layer that is formed on the metal molded body and contains the catalyst is accommodated in the reactor.

* * * * *